United States Patent
Luong et al.

(10) Patent No.: US 10,863,748 B2
(45) Date of Patent: Dec. 15, 2020

(54) ANTIBACTERIAL PRODUCTS AND PROCESSES FOR PREPARING ANTIBACTERIAL PRODUCTS FROM MAPLE SYRUP

(71) Applicants: John Ha-Thanh Luong, Montreal (CA); Gia-Tong Vuong, Hampstead (CA)

(72) Inventors: John Ha-Thanh Luong, Montreal (CA); Gia-Tong Vuong, Hampstead (CA)

(*) Notice: Subject to any disclaimer, the term of this patent is extended or adjusted under 35 U.S.C. 154(b) by 0 days.

(21) Appl. No.: 16/468,722

(22) PCT Filed: Dec. 8, 2017

(86) PCT No.: PCT/CA2017/051486
§ 371 (c)(1),
(2) Date: Jun. 12, 2019

(87) PCT Pub. No.: WO2018/107277
PCT Pub. Date: Jun. 21, 2018

(65) Prior Publication Data
US 2019/0357543 A1    Nov. 28, 2019

Related U.S. Application Data

(60) Provisional application No. 62/432,923, filed on Dec. 12, 2016.

(51) Int. Cl.
*A01N 65/08*    (2009.01)
(52) U.S. Cl.
CPC .................................. *A01N 65/08* (2013.01)
(58) Field of Classification Search
CPC ..................................................... A01N 65/08
See application file for complete search history.

(56) References Cited

U.S. PATENT DOCUMENTS

2013/0310332 A1* 11/2013 Barbeau ............... A23F 3/34
                                                        514/35
2016/0339071 A1   11/2016 Tunfenkji et al.
2018/0023217 A1    1/2018 Patton et al.

FOREIGN PATENT DOCUMENTS

WO         2012021983 A1     2/2012
WO         2012055010 A1     5/2012
WO     WO 2016/124926    * 11/2016

OTHER PUBLICATIONS

Jankovic (Hospital Pharmacology. 2014; 1(2):102-108).*
International Search Report and Written Opinion; International Application No. PCT/CA2017/051486; International Filing Date Dec. 8, 2017; dated Feb. 21, 2018 10 pages.
Maisuria et al.; "Polyphenolic Extract from Maple Syrup Potentiates Antibiotic Susceptibililty and Reduces Biofilm Formation of Pathogenic Bacteria"; Applied and Environmental Microbiology; 81(11); pp. 3782-3792; (2015).
Bi, W. et al.; "Traditional uses, phytochemistry, and pharmacology of the genus *Acer* (maple): A review"; Journal of Ethnopharmacology, vol. 189; 2016; ISSN 0378-8741; pp. 31-60.
Brown, A.; "Understanding Food: Principles and Preparation"; Cengage Learning, 4th edition; ISBN 978-0-538-73498-1; 2010; p. 441.
Buzid, A. et al.; "Molecular signature of pseudomonas aeruginosa with simultaneous nanornolar detection of quorum sensing signaling molecules at a boron-doped diamond electrode"; Scientific Reports, vol. 6, Article 30001; 2016; DOI: 10.1038/srep30001.
Canadian Food Inspection Agency; "Chapter 13—Labelling of Maple Products"; https://www.inspection.gc.ca/food-label-requirements/labelling/-f-for-industry/-f-maple-products/eng/1511931271546/1511931272231; 2011; 14 pages.
Fletcher et al.; "Biosensor-based assays for PQS, HHQ and related 2-alkyl-4-quinolone quorum sensing signal molecules"; Nature Protocols, vol. 2, issue No. 5; 2007; pp. 1254-1262.
Hammond, A.A. et al.; "An in vitro biofilm model to examine the effect of antibiotic ointments on biofilms produced by burn wound bacterial isolates"; Burns, vol. 37, Issue No. 2; 2011; pp. 312-321.
Jaiswal, A. et al.; "One step synthesis of C-dots by microwave mediated caramelization of poly(ethylene glycol)"; Chemical Communications, vol. 48, Issue No. 30; 2012; pp. 407-409.
Li, X. et al.; "Engineering surface states of carbon dots to achieve controllable luminescence for solid-luminescent composites and sensitive Be2+ detection"; Scientific Reports, vol. 4; 2014; p. 4976.
Nishioka, M. et al.; "Single mode microwave reactor used for continuous flow reactions under elevated pressure"; Industrial & Engineeing Chemistry Research, vol. 52, Issue No. 12; 2013; pp. 4683-4687.
Quebec Maple Syrup Producers Federation; "Grading System"; https://ppaq.ca/en/organization/quality/grading-system/; 2019; 4 pages.
Reen, F.J. et al.; "The Pseudomonas quinolone signal (PQS), and its precursor HHQ modulate interspecies and interkingdom behaviour"; FEMS Microbiology Ecology, vol. 77, Issue No. 2; 2011; pp. 413-428.
Shen, L. et al.; "The production of pH-sensitive photoluminescent carbon nanoparticles by the carbonization of polyethyleneimine and their use for bioimaging"; Carbon, vol. 55; 2013; pp. 343-349.
Statistical Overview of the Canadian Maple Industry 2017; Agriculture and Agri-Food Canada (AAFC); http://www.agr.gc.ca/eng/horticulture/horticulture-sector-reports/statistical-overview-of-the-canadian-maple-industry-2017/?id=1524607854094; Retrieved May 18, 2018; 11 pages.

(Continued)

*Primary Examiner* — Shirley V Gembeh
(74) *Attorney, Agent, or Firm* — Cantor Colburn LLP

(57) ABSTRACT

There is provided herein antibacterial products and processes for preparing antibacterial products from maple syrup and passivating agents in the presence of a catalyst under irradiation or hydrothermal reaction conditions. The disclosure further provides a method for inhibiting the growth of a gram-positive bacteria, a gram-negative bacteria or a yeast.

11 Claims, 8 Drawing Sheets

(56) References Cited

OTHER PUBLICATIONS

Taylor, F.H. et al.; "Variation in Sugar Content of Maple Sap"; Agricultural Experiment Station, University of Vermont and State Agricultural College; Bulletin 587; 1956; 41 pages.

Tsang, C.S. et al.; "Phospholipase, proteinase, and haemolytic activities of Candida aibicans isolated from oral cavities of patients with type 2 diabetes mellitus"; Journal of Medical Microbiology, vol. 56, Pt. 10; 2007; pp. 1393-1398.

Wang et al.; "Carbon quantum dots: synthesis, properties, and applications"; Journal of Material Chemistry, vol. 2; 2014; pp. 6921-6939.

Wu, L. et al.; "Surface passivation of carbon nanoparticles with branched macromolecules influences near infrared bioimaging"; Theranostics, vol. 3, Issue No. 9; 2013; pp. 677-686.

Yang, X. et al.; "Novel and green synthesis of high-fluorescent carbon dots originated from honey for sensing and imaging"; Biosensors and Bioelectronics, vol. 60; 2014; pp. 292-298.

Zhao, G, et al.; "Biofilms and inflammation in chronic wounds"; Advances in Wound Care, vol. 2, Issue No. 7; 2013; pp. 389-399.

Zhu, S. et al.; "Surface chemistry routes to modulate the photoluminescence of graphene quatum dots: from fluorescence mechanism to up-conversion bioimaging applications"; Advanced Functional Materials, vol. 22, Issue No. 22; 2012; pp. 4732-4740.

* cited by examiner

ANTIBACTERIAL PRODUCTS AND PROCESSES FOR PREPARING ANTIBACTERIAL PRODUCTS FROM MAPLE SYRUP

CROSS REFERENCE TO RELATED APPLICATIONS

This application is a National Stage Application of PCT/CA2017/051486, filed Dec. 8, 2017, which claims the benefit of U.S. Provisional Application No. 62/432,923, filed Dec. 12, 2016, both of which are incorporated by reference in their entirety herein.

FIELD OF THE DISCLOSURE

There is provided herein antibacterial products and processes for preparing antibacterial products from maple syrup and passivating agents in the presence of a catalyst under irradiation or hydrothermal reaction conditions.

BACKGROUND OF THE DISCLOSURE

Maple syrup is prepared from the xylem sap of sugar maple, red maple, black maple trees, as well as other maple species. However, the sugar maple (*Acer saccharum*), the black maple (*A. nigrum*), and the red maple (*A. rubrum*) are predominantly used to produce maple syrup due to their sugar content, ranging from 2 to 5% in the sap of these species. In cold climates during the winter, starch is stored in their trunks and roots and converted to sugar that rises in the sap in late winter and early spring. Sucrose, a disaccharide, is the most prevalent sugar in maple syrup. The sap's sugar content is variable within the same tree, ranging from 1.5% to 3.5% (Taylor, F H (1956). *Variation in Sugar Content of Maple Sap*. Agricultural Experiment Station, University of Vermont and State Agricultural College. Bulletin 587). The exuded sap is collected by drilling holes into their trunks and heated to evaporate the water, leaving the concentrated syrup.

In Canada, syrups must be made exclusively from maple sap with at least 66 percent sugar to qualify as maple syrup (*Statistical Overview of the Canadian Maple Industry 2014*. Agriculture and Agri-Food Canada (AAFC). Retrieved 18 May 2016). In other words, commercial maple syrup comprises 32% water by weight, 67% carbohydrates (90% of which are sugars), and no appreciable protein or fat. Maple syrup also has minute levels of minerals and trace amounts of amino acids. In the United States, a syrup must be made almost entirely from maple sap to be labeled as "maple" (Chapter 13 —*Labelling of Maple Products*. Canadian Food Inspection Agency. Retrieved 9 Dec. 2011). Maple syrup has a unique flavor and the chemistry of maple syrup is not fully characterized and understood (Brown A C (2010). *Understanding Food: Principles and Preparation*. Cengage Learning. p. 441. ISBN 978-0-538-73498-1).

Bacterial infection, in particular, chronic and acute wounds pose a major burden on healthcare systems with lengthy hospitalization and high mortality rate. In the United States alone, annual costs associated with chronic wounds are $25 billion (Zhao G, et al. (2013). *Biofilms and inflammation in chronic wounds*. Adv Wound Care 2, 389-399). Chronic wound infections are often associated with the formation of a biofilm, a polymer released by such infected bacteria to protect themselves from antibiotic treatment. Gram-positive *Staphylococcus aureus* (*S. aureus* and the gram negative *Pseudomonas aeruginosa* (*P. aeruginosa*) are often associated with wound infections (Hammond A A, et al. (2011). *An in vitro biofilm model to examine the effect of antibiotic ointments on biofilms produced by burn wound bacterial isolates*. Burns 37:312-321).

*Candida albicans* (*C. albicans*), a gram-positive yeast, is the commonest cause of candidiasis (moniliasis), a popular cause of oral and vaginal infections ("thrush"). *C. albicans* is polymorphic, i.e., it can grow as both a yeast and as filamentous cells, depending on the culture medium. *Escherichia coli* (*E. coli*) is a gram-negative, facultatively anaerobic, rod-shaped bacterium, i.e., it can grow under aerobic or anaerobic medium.

SUMMARY OF THE DISCLOSURE

An aspect of the disclosure relates to processes for preparing an antibacterial product comprising treating maple syrup and a passivating agent under irradiation or hydrothermal reaction conditions in the presence of a catalyst.

A further aspect of the disclosure relates to an antimicrobial product prepared by the process as defined herein.

A further aspect of the disclosure relates to an antimicrobial product as defined herein.

A further aspect of the disclosure relates to a method for inhibiting the growth of a gram-positive bacteria, a gram-negative bacteria or a yeast comprising contacting said bacteria or yeast with an antimicrobial product as defined herein.

DETAILED DESCRIPTION OF THE DISCLOSURE

Figure 1:
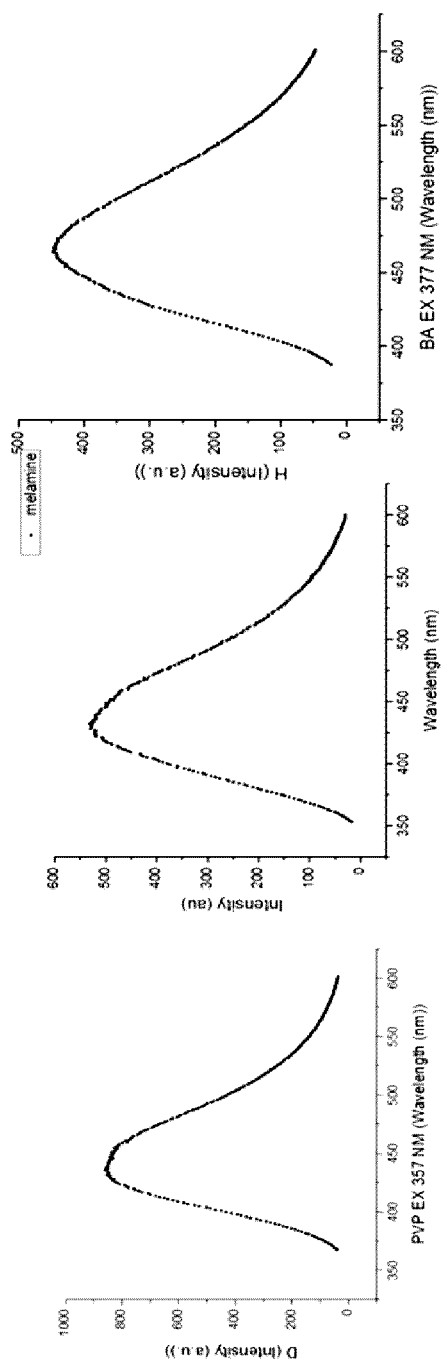
FIG. 1 is a representative fluorescence spectrum of products prepared by continuous microwave irradiation in accordance with embodiments herein.

This disclosure relates to the antimicrobial properties of products against both gram-positive and gram-negative bacteria and yeast. This disclosure further relates to the synthesis of a new class of antimicrobial products from maple syrup.

As described herein, antimicrobial products are prepared from maple syrup in the presence of a catalyst and passivating agents. The approach is environment-friendly and produced from edible materials.

The grading system of maple syrup is based on light transmission measured by a spectrophotometer. One grading system is defined as follows by the Québec Maple syrup Producers Federation: http://fpaq.ca/en/federation/quality/grading-system/:

| Category | % light transmission |
| --- | --- |
| Extra light | 100-75 |
| Light | 74.9-60.5 |
| Medium | 60.4-44 |
| Amber | 43.9-27 |
| Dark | 26.9-less |

The maple syrup to be used is not especially limited, however typical commercial syrups may contain about 17-18% carbohydrates. Typical commercial syrups may contain about 4-8% calcium, and in some cases up to 4-6% iron (Fe).

Although irradiation in the process described herein may be conducted with a domestic microwave reactor, other microwave reactors may be used while adjusting the reaction time and/or intensity of the microwave reactor. The irradiation under microwaves may be within frequencies from 0.3 to 300 GHz (corresponding wavelengths of 1 mm and 1 m). The commonly used frequency in a household microwave oven is 2.45 GHz with a wavelength of ~12.24 cm.

The hydrothermal treatment conditions may be adjusted. For example the reaction time and/or temperature may in practice be varied from about 60° C., to about 120° C. Although it may be possible to conduct the hydrothermal treatment under 60° C., the reaction may be sluggish and as such not be practical. Further, above 120° C., the product may become darker, and/or more viscous because of caramelization. In particular embodiments herein, the treatment was carried out for 1-2 h at a temperature ranging from 80-100° C.

In an embodiment, the process for preparing antimicrobial products are prepared from maple syrup in the presence of a catalyst such as hydrogen peroxide ($H_2O_2$). Other catalysts such as ascorbic acid, ethanol, and in particular concentrated acids (sulfuric acid, phosphoric acid, nitric acid, etc.) can be used. However, hydrogen peroxide is preferred over such acids because the resulting product does not require post-neutralization by an alkaline. Under the reaction conditions herein, hydrogen peroxide is advantageously decomposed to water and oxygen.

In an embodiment, the antimicrobial products are prepared from maple syrup in presence of passivating agents, such melamine, boric acid, or polyvinylpyrrolidone. Other passivating agents might be used, particularly nitrogen containing compounds such as polyethyleneimine, amino acids, urea, etc.

In one embodiment, the products have antimicrobial activity against gram-negative bacteria gram-positive bacteria, and yeasts.

In one embodiment, the products have antimicrobial activity against gram-negative bacteria gram-positive bacteria or yeasts.

In one embodiment, the products have antimicrobial activity against gram-negative bacteria such as *Escherichia coli* and *Pseudomonas aeruginosa*. The products are also active against other common gram-negative bacteria such as *Salmonella, Legionella, Neisseria gonorrhoeae* (sexually transmitted disease), *Campylobacter jejuni, Neisseria meningitides* (meningitis), *Moraxella catarrhalis-Haemophilus influenza* (respiratory symptoms) as well as bacteria associated with hospital-acquired infections include *Acinetobacter baumannii*, which cause bacteremia.

In one embodiment, the products have antimicrobial activity against gram-positive bacteria such as *Staphylococcus aureus, Streptococcus pneumoniae* (with reduced susceptibility to penicillins and macrolides), *Bacillus anthracis, Bacillus cereus, Clostridium botulinum, Enterococcus faecalis*, and *Listeria monocytogenes*.

In one embodiment, the products have antimicrobial activity against yeasts such as *Candida albicans, Pneumocystis jirovecii, Cryptococcus neoformans*, and other pathogenic fungi, e.g., *Exserohilum* and *Cladosporium*.

In one embodiment, the antimicrobial products are comprising passivated nanoparticles. In one embodiment, the antimicrobial products are comprising passivated nanoparticles with an average diameter of 100 nm (e.g. prepared with PVP) or nanoparticles ranging from 40-80 nm (e.g. prepared with melamine).

2. Synthesis and Characterization of Antibacterial Products
2.1 Materials and Chemicals.

Three different types of maple syrup were purchased from various local markets: light (light brown), medium (medium brown), and dark (dark brown) in color. The light maple syrup was a product of Bernard, Saint-Victor, Quebec, Canada). This product is labeled to contain 18% carbohydrates, 4% calcium, and 6% iron (Fe). The medium maple syrup was a product of President's Choices (Loblaws Inc, Toronto, Ontario, Canada). This product also has 18% carbohydrates and 8% calcium with a minute amount of proteins (0.1 g/200 mL). The dark maple syrup was purchased from President's Choices (Loblaws Inc, Toronto, Ontario, Canada). This product contains 17% carbohydrates, 8% calcium, and 4% iron.

Hydrogen peroxide ($H_2O_2$, 30% weight/weight), melamine ($C_3H_6N_6$, 99%, 2,4,6-triamino-1,3,5-triazine or triaminotriazine, molecular weight=126.12), boric acid (>99.5%, $H_3BO_3$, molecular weight=61.83) and polyvinylpyrrolidone (PVP, polyvidone or povidone, $[C_6H_9NO]_n$, average molecular weight of 10 kDa and 40 kDa) were purchased from Sigma-Aldrich.

*Escherichia coli* (*E. coli*) ATCC 25922 and *Staphylococcus aureus* (*S. aureus*) ATCC 29213 were obtained from American Type Culture Collection (ATCC, Manassas, Va., USA). *E. coli* ATCC 35922 does not produce verotoxin, however, it is a CLSI (Clinical and Laboratory Standard Institute, 950 West Valley Road, Suite 2500, Wayne, Pa. 19087 USA) control strain for antimicrobial susceptibility and media testing. *S. aureus* ATCC 29213 is considered as one of the methicillin-sensitive *Staphylococcus* (MSS) research materials. *Pseudomonas aeruginosa* (*P. aeruginosa*, PA) PA14 was obtained from the Institute of Microbiology, University College Cork, Cork, Ireland. PA is a gram-negative pathogenic bacterium associated with hospital-acquired infections, particularly in patients with compromised immunity. Further information of this pathogenic bacterium can be found elsewhere (Buzid A et al. (2016). *Molecular signature of Pseudomonas aeruginosa with simultaneous nanomolar detection of quorum sensing signaling molecules at a boron-doped diamond electrode*. Nature: Sci. Rep. 6, article 30001). *Candida albicans* (strain SC5314) is also designated as ATCC MYA-2876. *Candida albicans* is an opportunistic human fungal pathogen and is responsible for candidiasis.

2.2 Synthesis of Antibacterial Products.

Two different procedures were conducted to antibacterial products from maple syrup: irradiation under a microwave oven and hydrothermal reaction. In both cases, the reaction liquids contain 2 g maple syrup (0.36 g carbohydrates), 2 mL hydrogen peroxide (30% w/w), 0.2 g melamine, boric acid, or PVP. Deionized water was added to adjust the total volume to 10 mL. Thus, the starting reaction liquid comprises (g/mL) 0.036 carbohydrates, 0.06 hydrogen peroxide, and 0.02 melamine, boric acid or PVP.

The irradiation of the content was conducted for 1-2 min at 100% power (cycle mode of 21 s "ON" and 9 s "OFF"). The output of the domestic microwave reactor was 1100 W. A cooling coil was mounted on the reaction flask, enabling the passing of cooling water through the coil to regulate the temperature of the reaction liquid. The initial color of the reaction liquid comprising maple syrup (medium color), polyvinylpyrrolidone, and hydrogen peroxide (before continuous microwave irradiation) was essentially that of the maple syrup.

At the end of the reaction, the temperature of the mixture was measured by a pyrometer and was about 60° C. The resulting reaction liquid was cooled by convection at room temperature and subjected to further characterization and antimicrobial testing.

Microwave irradiation of organic compounds is a rapid and low-cost method to synthesize carbon materials and carbon dots from different precursors (Jaiswal A et al. (2012). *One step synthesis of C-dots by microwave mediated caramelization of poly(ethylene glycol)*. Chem. Commun. 48, 407-409). Microwaves are the electromagnetic waves with frequencies from 0.3 to 300 GHz and corresponding wavelengths of 1 mm and 1 m. However, the commonly used frequency in a household microwave oven is 2.45 GHz with a wavelength of ~12.24 cm. Although the raising temperature profile is volume dependent, microwave irradiation often raises the temperature of the whole reaction volume simultaneously within 1 min.

Microwave irradiation using a flow cell is also commercially available, an interesting approach to accommodate large volumes of materials. A continuous flow-type microwave reactor described by Nishioka et al. (Nishioka M et al. (2013). *Single mode microwave reactor used for continuous flow reactions under elevated pressure*. Ind. Eng. Chem. Res. 52, 4683-4687) is suitable for the rapid and scaling up the synthesis of nanostructured materials. The system is equipped with a pressurized function allowing homogeneous heating of the reaction solution flow.

The hydrothermal catalytic reactions were performed in water using a stainless steel Teflon-lined hydrothermal synthesis reactor (100 mL, stainless-steel autoclave with a polytetrafluoroethylene (PTFE) hydrothermal synthesis reactor). This is a product of Tefic Biotech Ltd (Shaanxi, China). The hydrothermal treatment was carried out for 1-2 h in the temperature range of 80-100° C. The experimental conditions (reaction duration and temperature) were varied to find the best optimal conditions as reflected by the properties of organic nanoparticles synthesized. After the reaction was completed, the reaction liquid was quenched by natural convection cooling to the room temperature.

Hydrothermal carbonization, also known as solvothermal carbonization, is a low cost, and nontoxic procedure for the synthesis of carbon-based materials from different precursors such as glucose, citric acid, chitosan, proteins, etc. The procedure is also simple since a solution of the organic precursor is only sealed and reacted in a hydrothermal reactor at moderately high temperature.

2.3 Characterization of the Antibacterial Products.

UV-Vis spectra of the resulting liquid were recorded using a Cary 100 scan Varian UV/Vis spectrophotometer. Fluorescence emission studies were performed using a fluorescence spectrophotometer (Varian Cary Eclipse) equipped with a 120 W Xenon lamp as the excitation source. The following parameters were used to acquire the fluorescence spectra: scan rate=600 nm/s, excitation slit=5 nm and emission slit=5 nm.

Zeta potential measurements were performed using a Zetasizer Nano ZS (ZEN3600 Malvern Instruments, UK). TEM samples were prepared and analyzed by a JEOL 2100 TEM operating at 200 kV.

2.4 Culture Medium and Cell Growth.

Cultures of *E. coli* ATCC 25922 or *S. aureus* ATCC 29213 were grown in the Luria-Bertani (LB) medium at 37° C. for 15-17 h. The medium comprises tryptone 10 g, yeast extract 5 g, and 10 g NaCl in 950 mL of deionized water. Deionized water was then added to adjust the final volume of the solution to 1 liter. The medium was then sterilized by autoclaving for 20 min at 15 psi (1.05 kg/cm$^2$) on liquid cycle. The overnight bacterial culture growth was quantified by the absorbance at 595 nm and diluted to 10$^8$ CFU/ml.

The overnight bacterial culture of *P. aeruginosa* PAO1 was transferred into a fresh (LB) broth (OD$_{600\ nm}$=0.05) using a modified version of the protocol described by Fletcher et al. (Fletcher M P et al. (2007). *Biosensor-based assays for PQS, HHQ and related 2-alkyl-4-quinolone quorum sensing signal molecules*. Nat. Protoc. 2, 1254-1262).

*C. albicans* cells were grown as yeast cultures at 30° C. overnight in non-filament-inducing medium, YPD (2% w/v Bacto peptone, 1% w/v yeast extract and 2% w/v glucose). Further information on the growth of *C. albicans* can be found elsewhere (Reen F J et al. (2011). *The Pseudomonas quinolone signal (PQS), and its precursor HHQ modulate interspecies and interkingdom behaviour*. FEMS Microbiol. Ecol. 77, 413-428).

2.5 Antimicrobial Assays.

The minimum inhibitory concentration of the samples was investigated against *E. coli* and *S. aureus*. Both strains were grown aerobically overnight at 37° C. in LB broth for 12-16 hours. The absorbance at 600 nm (wavelength) of the overnight grown cultures was measured and a final bacterial concentration of 10$^8$ colony forming unit per milliliter (CFU/mL) was achieved. 500 µL of the inoculum is added to each dilution tube. The sample solution (500 µL) was added to the first tube and then gradually diluted in subsequent tubes. The tubes were incubated at 37° C. for 24 hours by shaking on a rotary shaker at 150 shakes per min. After 24 hours of incubation, the cultures were confirmed for any plausible growth using viable cell count method. An aliquot of 100 µL each was taken and diluted tenfold in 20% LB medium, and then transferred onto nutrient agar plates. The plates were incubated overnight and then counted for viable bacteria. The viable bacteria were monitored by the CFU method from the appropriate dilution on nutrient agar plates.

The experiments were then extended to assess the antimicrobial properties of the prepared maple syrup samples for four microorganisms. In this case, the agar diffusion test was also performed with some modifications. In brief, overnight cultures of four test strains *P. aeruginosa* PA14, *S. aureus*, *E. coli* MUH, and *C. albicans* SC5314 were diluted to Abs$_{600\ nm}$ of 0.02. These were swabbed on Mueller-Hinton (MH) agar (better diffusion than LB) plates for the three bacteria and left to dry in a laminar hood. Yeast peptone dextrose (YPD) plates were used to test *Candida albicans* SC5314. Biological triplicates reps of all test strains were used. Wells were created using sterile blue tips, and 75 µL of each compound was added to the wells. Plates were incubated overnight at 37° C. and visualized for growth inhibition the following day.

In corroboration with the agar diffusion test, the antibacterial activities of all three liquids prepared from maple syrup with PVP, melamine or boric acid were measured in liquid culture in microtiter plates using a BioScreen C analyzer (Oy Growth Curves Ab Ltd, Helsinki). As microorganisms grow, they increase the turbidity of their growth medium. The absorbance of the growth medium can be measured over time to reflect the microbial growth or any inhibition effected by the prepared maple syrup samples.

3. Properties of the Antibacterial Products 3.1 General Observations.

The initial reaction liquid exhibited the color of the type of maple syrup used but the color was somewhat lighter due to the dilution with hydrogen peroxide and deionized water. The reaction liquid was forcefully mixed within 10 s into the experiment with continuous microwave irradiation. After 1-2 minutes of irradiation in the presence of hydrogen peroxide and boric acid or melamine, the color of the resulting liquid was almost transparent. In contrast, the resulting liquid with PVP still retained the yellow color under ambient light. Both hydrothermal treatment and microwave irradiation offered similar products as attested by fluorescence spectra as addressed later. Under UV light, all three resulting liquids exhibited fluorescence: dark green with PVP and blue for melamine or boric acid. Considering sucrose as the major component of maple syrup, the experiment with pure sucrose together with PVP, melamine or boric acid in the presence of hydrogen peroxide did not result in the liquids with any detectable fluorescence.

3.2 Fluorescence Properties of Antibacterial Products.

The fluorescent properties of the resulting liquids were then investigated and exhibited a maximum excitation peak at around 357 nm, 357 nm, and 377 nm, respectively for the reaction liquid prepared with PVP, melamine, or boric acid (FIG. 1). These excitation wavelengths were then used to search for the maximum emission wavelength of the resulting reaction liquids. As shown in FIG. 1 (left), the resulting liquid prepared from PVP or melamine exhibited a maximum emission length at around 425 nm. The reaction liquid prepared with boric acid had a maximum emission peak at 470 nm. Without hydrogen peroxide, no fluorescence signal was observed and both the medium and dark (in color) maple syrup behaved similarly with respect to the excitation wavelength, the emission wavelength, and the fluorescence intensity. The light (in color) maple syrup exhibited very weak fluorescence signals FIG. 1 (right).

Figure 2:
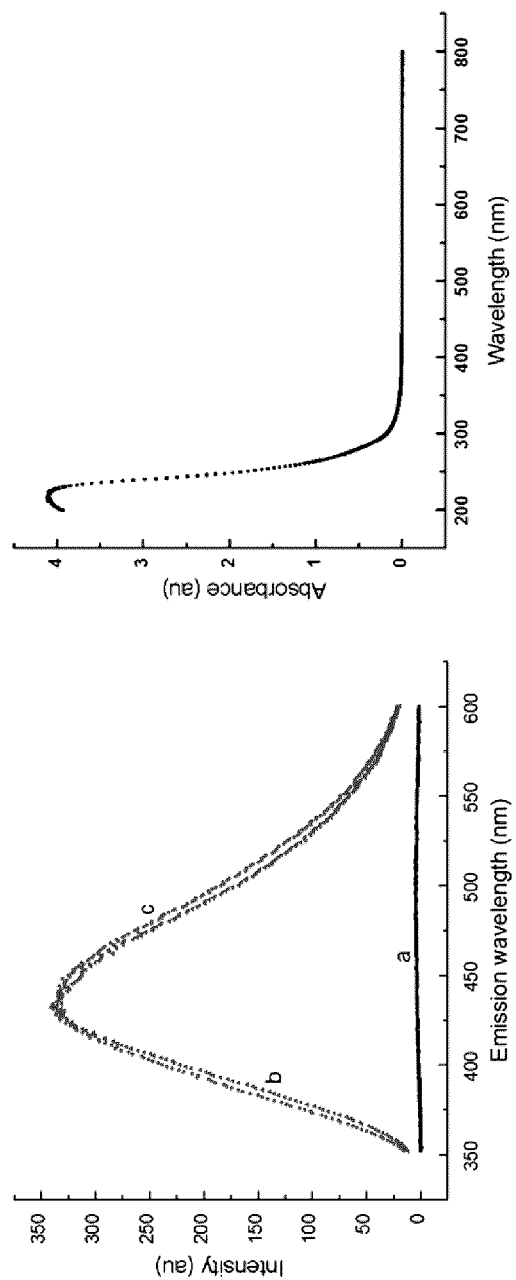
FIG. 2 illustrates the fluorescence spectrum (left) and absorption spectrum (right) of the reference starting material as well as products prepared by continuous microwave irradiation in accordance with embodiments herein.

The optical absorption of all three resulting liquids was virtually featureless as shown in FIG. 2 for a representative spectrum. FIG. 2 (Left) illustrates the fluorescence intensity of the resultant liquid prepared from maple syrup with medium color together with polyvinylpyrrolidone without hydrogen peroxide (curve a), with hydrogen peroxide (curve c), and maple syrup with a dark color (curve b). FIG. 2 (Right) represents the absorption spectrum of the resultant liquid prepared from maple syrup (medium color) together with PVP and hydrogen peroxide. The products were prepared by continuous microwave irradiation for 1 min. The resultant liquids retained their fluorescence intensity after several months when stored at room temperature.

3.3 TEM Micrographs and Zeta Potential Measurement.

Figure 3:
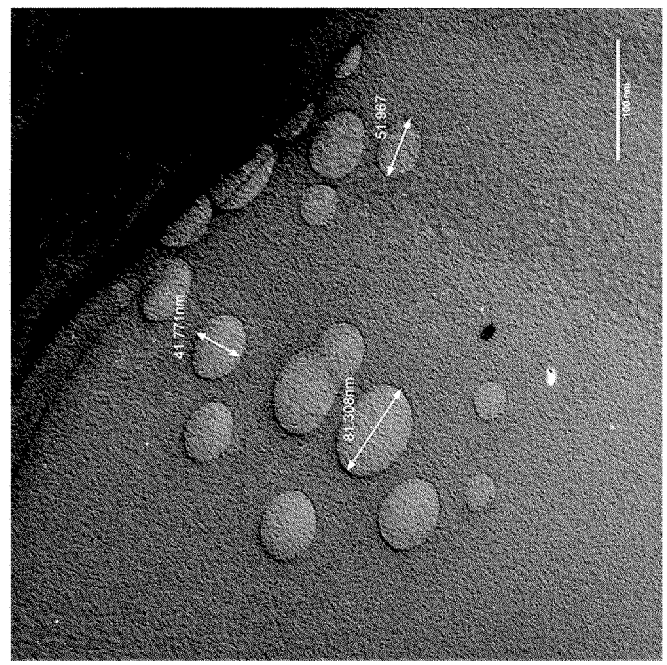
FIG. 3 presents the TEM micrographs of products prepared by continuous microwave irradiation in accordance with embodiments herein.
Figure 3:
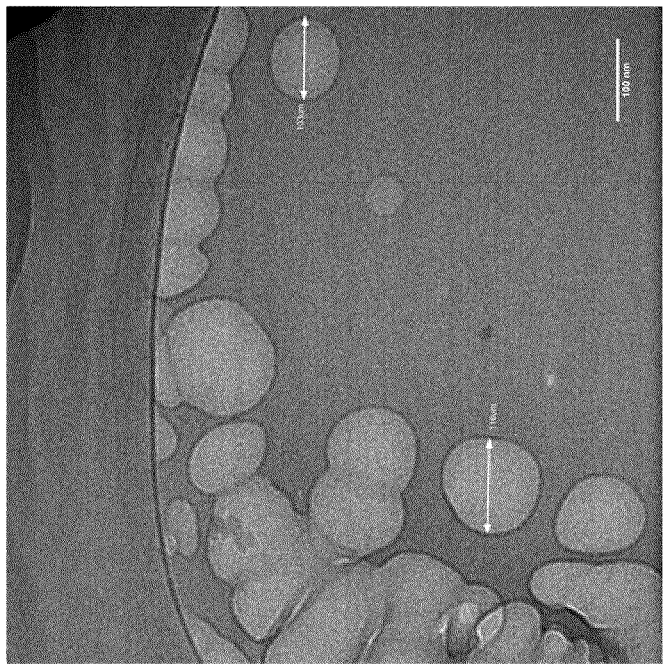

FIG. 3 are TEM micrographs of products in accordance with the present disclosure prepared by continuous microwave irradiation for 1 min.

TEM revealed that the resulting reaction liquid prepared with PVP from continuous microwave irradiation for 1 min contains nanoparticles with an average diameter of 100 nm (FIG. 3 (left)). The liquid prepared from melamine also contains nanoparticles, ranging from 40-80 nm (FIG. 3 (right)) whereas the one prepared with boric acid contains no nanoparticles.

The formation of nanoparticles deserves a brief comment here since strong oxidizing acids can carbonize small organic molecules to carbonaceous materials, which can be further cut into small sheets by controlled oxidation (Shen L et al. (2013). *The production of pH-sensitive photoluminescent carbon nanoparticles by the carbonization of polyethyleneimine and their use for bioimaging*. Carbon 55, 343-349). Microwave irradiation of organic compounds is a low-cost method to synthesize carbon dots (CDs), normally with an average diameter of less than 10 nm (Wang Y F et al. (2014). *Carbon quantum dots: synthesis, properties, and applications*. J. Mater. Chem. C 2, 6921-6939). In particular, CDs with a diameter of 2 nm has been synthesized from honey and hydrogen peroxide by hydrothermal treatment for 2 h at 100° C. (Yang X et al. (2014). *Novel and green synthesis of high-fluorescent carbon dots originated from honey for sensing and imaging*. Biosensors Bioelectronics 60, 292-298). The emission peaks of such CDs shift to longer wavelength and the fluorescence intensity decreases with the excitation wavelength varying from 320 nm to 410 nm. However, the UV-vis absorption spectrum has a peak at 278 nm owing to n-$\pi^*$ transition of C=O and $\pi$-$\pi^*$ transition of C=C. Such absorption features are not observed with the nanoparticles prepared from maple syrup as described earlier.

Zeta potential measurement indicated that the resulting liquid prepared from PVP exhibited a slight negative charge of −0.23 mV comparable to −0.17 mV for the counterpart prepared with πmelamine. The zeta potential of the sample prepared with boric acid has a more negative potential of −0.5 mV.

In contrast, carbon dots prepared from honey and branched polymers with hydroxyl groups have considerably higher zeta potential values, −10 to −38 mV with the hydrodynamic size in aqueous suspension is within 8-20 nm (Wu L et al. (2013). *Surface passivation of carbon nanoparticles with branched macromolecules influences near infrared bioimaging*. Theranostics 3(9), 677-686). The majority of CDs are rich in oxygen-containing groups such as —OH, =O, —COOH, etc., this a negative surface charge is generally observed for such CDs.

In this specification, the surface of organic nanoparticles was passivated by PVP or melamine by ionic interaction, $\pi$-$\pi$ stacking, hydrophobic interaction, hydrogen bonding, etc. to render the surface close to neutral. The amino groups of melamine might form covalent bonding with —COH of carbohydrates and other organic compounds present in maple syrup.

Figure 4:
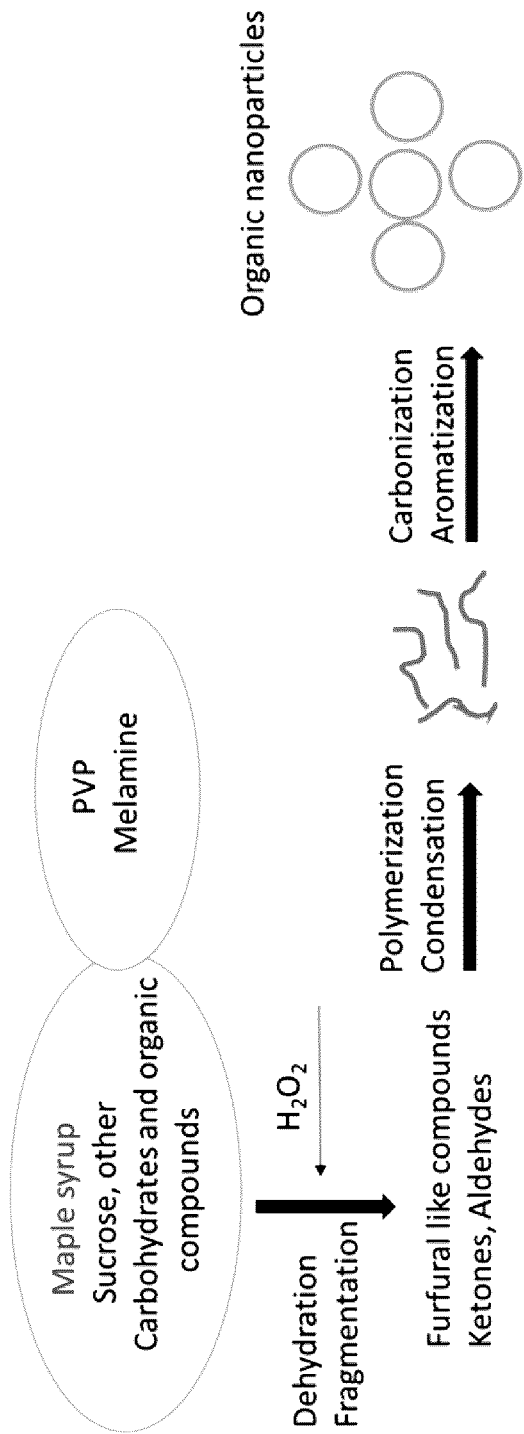
FIG. 4 is a schematic representation of a possible mechanism for the preparation of products in accordance with embodiments herein.

On the basis of such results and observation, a mechanism is proposed pertaining to the formation of organic nanoparticles (FIG. 4). In brief, the substrates consisting of carbohydrates and organic molecules or maple syrup together with PVP or melamine have undergone dehydration and fragmentation under microwave irradiation or hydrothermal treatment to form furfural, ketones, and aldehydes in the presence of hydrogen peroxides. Such intermediates were then subjected to polymerization and condensation followed by carbonization and aromatization to form organic nanoparticles. PVP or melamine was passivated on the surface of nanoparticles via ionic/hydrophobic interactions, π-π stacking, etc. to form stable complexes.

The amino group of melamine might form covalent bonds with —COOH on the surface of organic nanoparticles (Li X, et al. (2014). *Engineering surface states of carbon dots to achieve controllable luminescence for solid-luminescent composites and sensitive $Be^{2+}$ detection*. Scientific Reports 4: 4976). Nitrogen-containing organic compounds with short chains are often used as effective passivating agents (Zhu S et al. (2012). *Surface chemistry routes to modulate the photoluminescence of graphene quantum dots: from fluorescence mechanism to up-conversion bioimaging applications*. Adv. Funct. Mater. 22, 4732-4740).

4. Antimicrobial Test.

4.1. Plate-Based Antibacterial Assays for *Staphylococcus aureus* and *Escherichia coli*.

Figure 5:
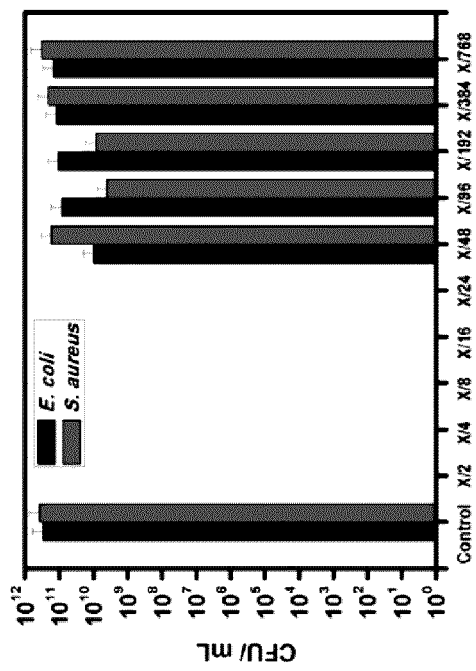
FIG. 5 is a bar graph of viable cell counts of *E. coli* and *S. aureus* after their exposure to products in accordance with this disclosure.
Figure 5:
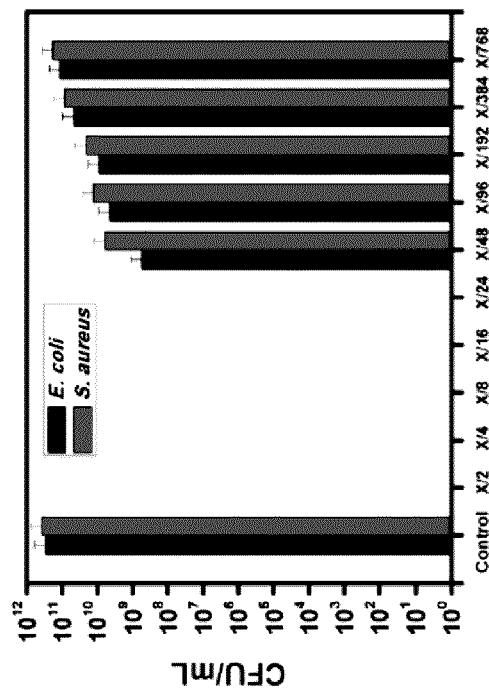

FIG. 5 is a bar graph of viable cell counts of *E. coli* and *S. aureus* after their exposure to products in accordance with this disclosure, prepared from maple syrup (medium in color) together with hydrogen peroxide. (Left) with melamine and (Right) with polyvinylpyrrolidone. No viable cells of *S. aureus* and *E. coli* were observed on the LB agar plates even the syrup samples were diluted 24-folds. Cell growth, however, were observed with increasing dilution of the tested maple syrup ranging from suppressed growth to no alteration in growth (FIG. 5). The starting maple syrup per se (without modification and any dilution) did not suppress the growth of these two bacteria. The liquid prepared with melamine appeared to have a noticeably stronger detrimental effect on *E. coli* and *S. aureus* compared to the counterpart prepared with polyvinylpyrrolidone.

4.2 Plate-Based Antibacterial Assays for *Pseudomonas aeruginosa* PA14, *Staphylococcus aureus* and *Escherichia coli* MUH (Mercy University Hospital, Cork, Ireland).

Initially, overnight cultures of test strains *Pseudomonas aeruginosa* PA14, *Staphylococcus aureus* and *Escherichia coli* MUH were diluted to $Abs_{600\ nm}$ of 0.02. These were swabbed on LB plates and left to dry in a laminar hood. Biological triplicates reps of all test strains were used. Wells were created using sterile blue tips, and 75 μL of each compound prepared from the maple syrup was added to the wells. Plates were incubated overnight at 37° C. and visualized for growth inhibition the following day. Initial analysis revealed antibacterial activity by all three resultant maple syrup samples prepared with PVP, melamine, and boric acid.

Subsequently, the plate assays were repeated using Mueller-Hinton (MH) agar to provide better diffusion than LB agar), as well as using Yeast Peptone Dextrose (YPD) plates to test *Candida albicans* SC5314. In brief, Mueller-Hinton agar contains (g/L) beef extract (2), acid hydrolysate of casein (17.5), starch (1.5) and agar (17). Deionized water is added to attain 1000 mL. Both beef extract and acid hydrolysate of casein provide nitrogen, vitamins, carbon, amino acids, sulfur, and other essential nutrients to support the microbial growth. Starch is added to absorb any toxic metabolites produced. Starch is also hydrolyzed to yield dextrose as a source of carbon whereas agar is the solidifying agent. The MH agar is more commonly used for the routine susceptibility testing of non-fastidious microorganism by the Kirby-Bauer disk diffusion technique.

Overnight cultures (three biological replicates) were diluted to $1\times10^5$ CFU/mL and swabbed as before. Aliquots of 50 μL of the maple syrup samples were added to the wells and plates were incubated at 37° C. overnight.

Figure 6:
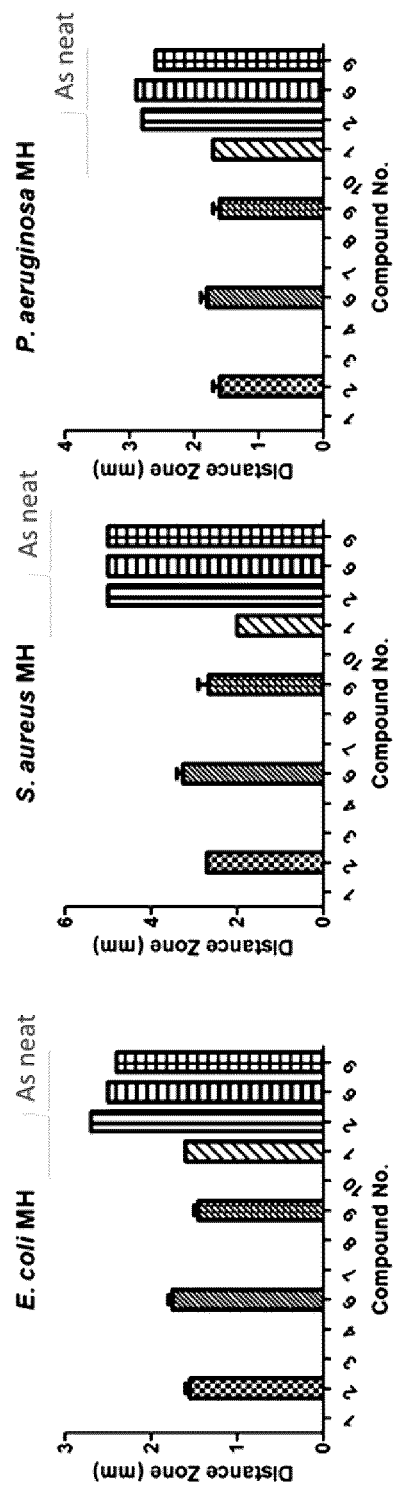
FIG. 6 is a bar graph showing the results of bacterial strains grown on MH plates.

Results are displayed in FIG. 6 with bacterial strains grown on MH plates. Compound no. (1) prepared with polyvinylpyrrolidone, (2) prepared with melamine, and (6, 9) prepared with boric acid. The samples 1, 2, and 6 were prepared by microwave irradiation whereas sample 9 was prepared by hydrothermal reaction. The letters MH mean Mueller-Hinton agar as described in the text. The Y-axis represents the zone of inhibition.

Compounds 2, 6, and 9 showed activity when diluted 1:25 (three separate columns from the left). Compounds 1, 2, 6, and 9 were active when used as neat (without dilution, a cluster of the four columns from the right). The experimental data confirmed that all maple syrup samples as neat (without dilution) exhibited antimicrobial activity against *E. coli, S. aureus,* and *P. aeruginosa* (FIG. 6). The maple syrup samples prepared from melamine or boric acid exhibited antimicrobial activity against the three above bacteria when they were diluted 25 folds. The diluted sample prepared with PVP was not effective.

Figure 7:
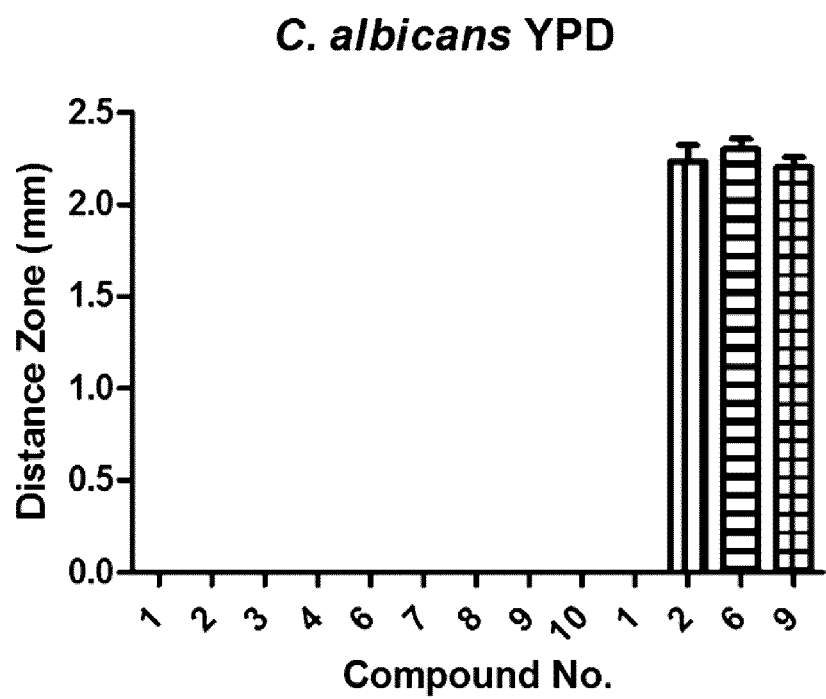
FIG. 7 is a bar graph showing the results for *C. albicans* growth on YPD plates.

FIG. 7 is a bar graph showing the results for *C. albicans* growth on YPD plates. Compound no. (1) prepared with PVP, (2) prepared with melamine, and (6, 9) prepared with boric acid. The samples 1, 2, and 6 were prepared by microwave irradiation whereas sample 9 was prepared by hydrothermal reaction. The letter YPG means yeast extract, peptone, and glucose (dextrose) plates. Compounds 1, 2, 6, and 9 are presented as 1:25 dilutions on the left series, and as neat on the right.

Samples 2, 6, and 9 displayed antifungal activity against *C. albicans* (FIG. 7). This activity was absent however when the samples were diluted 25-folds. In this assay, sample 1, prepared with PVP was not effective. The samples prepared with melamine or boric acid were comparable with respect to its antimicrobial and antifungal activity against the above three bacteria and one yeast. As expected, both samples (6) and (9) were comparable as they were prepared with boric acid by microwave irradiation and hydrothermal treatment, respectively.

It should be important to note that melamine per se did not exhibit any antimicrobial effect, possibly due to its poor aqueous solubility (3.2 g/L).

4.3. Liquid-Based Growth Kinetic Assays.

Figure 8:
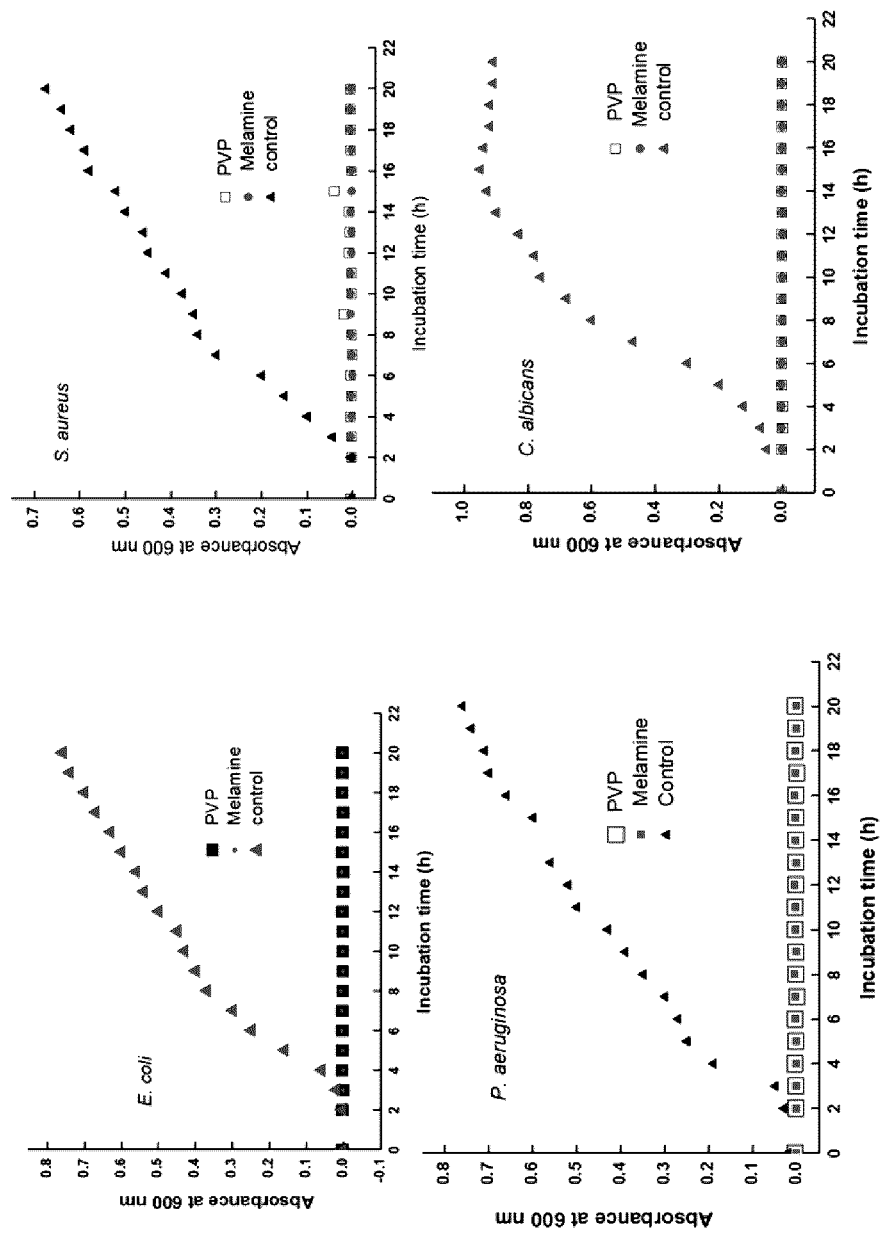
FIG. 8 shows the results obtained with *E. coli, S. aureus*, and *P. aeruginosa* and YPD (*C. albicans*) growth kinetics in the presence of samples prepared as described herein.

A series of experiments was conducted to perform liquid based growth assays to monitor the effect of each compound on the growth kinetics of the test organisms. Cells were diluted to $1\times10^5$ CFU/mL and added to the wells of honeycomb plates in 190 μL aliquots. Aliquots of compounds (10 μL) of the maple syrup samples were then added and growth was monitored at 37° C. static, with shaking for 10 s before absorbance reading (also known as optical density in the past) every hour for a period of 20 h (FIG. 8). FIG. 8 shows the results obtained with *E. coli, S. aureus,* and *P. aeruginosa* and YPD (*C. albicans*) growth kinetics in the presence of samples prepared as described herein. All compounds were added as neat (without dilution) to the culture. Data represents a minimum of two biological replicates for each data point. MH: Mueller-Hinton media and YPD: yeast, peptone, and dextrose (glucose) media.

All four compounds 1, 2, 6, and 9 suppressed the growth of the test microorganisms as expected based on the agar plate assays. It should be noted that the data obtained for the samples prepared from boric acid were not included in FIG. 8 since they were overlapped with the data obtained for the samples prepared with PVP or melamine. During the course of the cell growth for 20 h, the absorbance measured at 600 nm remained unchanged and fluctuated around the baseline value of 0.005. Such a result attested that the cell growth was completely inhibited by the sample prepared with boric acid using microwave irradiation or hydrothermal reaction.

In particular, the antifungal activity of the prepared maple syrup against *C. albicans* is appealing considering the resistance to antifungal drugs by fast changing strains of *C. albicans*. The treatment of candidiasis is more challenging when the infection occurs in patients with diabetes and high blood pressure (Tang C S et al. (2007). *Phospholipase, proteinase, and haemolytic activities of Candida albicans isolated from oral cavities of patients with type 2 diabetes mellitus*. J. Med. Microbiol. 56(pt10), 1393-1998), two common diseases in our modern society as well as immunocompromised population. Another important feature is the antimicrobial activities against both gram negative and positive bacteria. In general, it is difficult to treat gram-negative bacteria in comparison to gram-positive bacteria since a membrane present around the cell wall of gram-negative bacteria increases the risk of toxicity to the host but this membrane is absent in gram-positive bacteria. Porin channels in gram-negative bacteria also prevent the entry of harmful chemicals and antibiotics like penicillin. The risk of resistance against antibiotics is more in gram-negative bacteria due to the presence of external covering the cell wall.

All references cited herein are hereby incorporated by reference in their entirety.

The invention claimed is:

1. A process for preparing an antimicrobial product, comprising treating a composition comprising maple syrup and a passivating agent under irradiation or hydrothermal reaction conditions in the presence of a catalyst, wherein passivating agent is melamine or polyvinylpyrrolidone and the catalyst is hydrogen peroxide ($H_2O_2$), ascorbic acid, or a concentrated acid.

2. The process of claim 1, wherein said irradiation is a microwave irradiation within a frequency ranging from 0.3 to 300 GHz.

3. The process of claim 1, wherein said hydrothermal reaction is conducted at a temperature from about 60° C., to about 120° C.

4. The process of claim 1, wherein said concentrated acid is sulfuric acid, phosphoric acid or nitric acid.

5. The process of claim 1, wherein said antimicrobial product is a passivated nanoparticle having an average diameter of 100 nm when the passivating agent is polyvinylpyrrolidone (PVP), or a passivated nanoparticle having an average diameter ranging from 40-80 nm when the passivating agent is melamine.

6. An antimicrobial product prepared by the process as defined in claim 1.

7. The antimicrobial product of claim 6, wherein said product is a passivated nanoparticle having an average diameter of 100 nm when the passivating agent is polyvinylpyrrolidone (PVP), or a passivated nanoparticle having an average diameter ranging from 40-80 nm when the passivating agent is melamine.

8. A method for inhibiting the growth of a gram-positive bacteria, a gram-negative bacteria or a yeast, comprising contacting said bacteria or yeast with an antimicrobial product; wherein said antimicrobial product is prepared by the process as defined in claim 1.

9. The method of claim 8, wherein said gram-negative bacteria is *Escherichia coli, Pseudomonas aeruginosa Salmonella, Legionella, Neisseria gonorrhoeae, Campylobacter jejuni, Neisseria meningitides, Moraxella catarrhalis-Haemophilus* influenza, or *Acinetobacter baumannii*.

10. The method of claim 8, wherein said gram-positive bacteria is *Staphylococcus aureus, Streptococcus pneumoniae* with reduced susceptibility to penicillins and macrolides, *Bacillus anthracis, Bacillus cereus, Clostridium botulinum, Enterococcus faecalis*, or *Listeria monocytogenes*.

11. The method of claim 8, wherein said yeast is *Candida albicans, Pneumocystis jirovecii, Cryptococcus neoformans, Exserohilum*, or *Cladosporium*.

* * * * *